(12) United States Patent
Makino et al.

(10) Patent No.: US 8,771,231 B2
(45) Date of Patent: Jul. 8, 2014

(54) CATHETER FIXATION DEVICE

(75) Inventors: Masanori Makino, Shizuoka-ken (JP); Kazuhiro Koike, Shizuoka-ken (JP)

(73) Assignee: Covidien LLP, Mansfield, MA (US)

( * ) Notice: Subject to any disclaimer, the term of this patent is extended or adjusted under 35 U.S.C. 154(b) by 0 days.

(21) Appl. No.: 13/595,094

(22) Filed: Aug. 27, 2012

(65) Prior Publication Data
US 2013/0079722 A1    Mar. 28, 2013

(30) Foreign Application Priority Data

Sep. 28, 2011 (JP) .................................. 2011-213481

(51) Int. Cl.
*A61M 5/32* (2006.01)

(52) U.S. Cl.
USPC ............ 604/174; 604/177; 604/180; 604/175

(58) Field of Classification Search
USPC ........... 604/174–175, 177–180; 206/363, 364
See application file for complete search history.

(56) References Cited

U.S. PATENT DOCUMENTS

| | | | |
|---|---|---|---|
| 4,170,995 A | 10/1979 | Levine et al. | |
| 4,224,937 A | 9/1980 | Gordon | |
| 4,250,880 A | 2/1981 | Gordon | |
| 4,397,647 A | 8/1983 | Gordon | |
| 4,449,975 A | 5/1984 | Perry | |
| 4,460,356 A | 7/1984 | Moseley | |
| 4,490,141 A | 12/1984 | Lacko et al. | |
| 4,527,559 A | 7/1985 | Roxburg et al. | |
| 4,563,177 A | 1/1986 | Kamen | |
| 4,678,462 A | 7/1987 | Vaillancourt | |
| 4,698,057 A | 10/1987 | Joishy | |
| 4,737,143 A | 4/1988 | Russell | |
| 4,808,162 A | 2/1989 | Oliver | |
| 4,820,274 A | 4/1989 | Choksi | |
| 4,826,486 A | 5/1989 | Palsrok | |
| 4,863,432 A | 9/1989 | Kvalo | |
| 4,898,587 A | 2/1990 | Mera | |
| 4,976,698 A | 12/1990 | Stokley | |

(Continued)

FOREIGN PATENT DOCUMENTS

| | | |
|---|---|---|
| CN | 201008697 | 1/2008 |
| EP | 1 048 320 | 11/2000 |

(Continued)

OTHER PUBLICATIONS

U.S. Appl. No. 13/595,052, filed Aug. 27, 2012, Mizoguchi et al.

(Continued)

*Primary Examiner* — Edelmira Bosques
(74) *Attorney, Agent, or Firm* — John Paul Mello, Esq.

(57) ABSTRACT

A catheter fixture 11 for fixing a tubular catheter 1 to skin of a patient is provided with a plate shaped fixture main body 21, a fixing member 41 that is configured separately from the fixture main body, and a pivot connecting shaft 45. The plate shaped fixture main body 21 includes a retention part 22 where a catheter retaining groove 25 is formed, and a pair of winged pieces 23*a* and 23*b*. The pivot connecting shaft 45 both connects the fixture main body 21 and the fixing member 41 and acts as the pivot access C1 of the fixing member 41. The fixing member 41 has a pivoting action along a horizontal plane direction of the fixture main body 21 centrally around the pivot connecting shaft 45. When doing so, the catheter retaining groove 25 is covered by the fixing member 41 thereby fixing the catheter 1.

5 Claims, 5 Drawing Sheets

(56) References Cited

U.S. PATENT DOCUMENTS

| | | | |
|---|---|---|---|
| 4,981,475 | A | 1/1991 | Haindl |
| 5,084,026 | A | 1/1992 | Shapiro |
| 5,215,532 | A | 6/1993 | Atkinson |
| 5,300,037 | A | 4/1994 | Delk et al. |
| 5,306,256 | A | 4/1994 | Jose |
| 5,314,411 | A | 5/1994 | Bierman et al. |
| 5,344,415 | A | 9/1994 | DeBusk |
| 5,354,282 | A | 10/1994 | Bierman |
| 5,372,589 | A | 12/1994 | Davis |
| 5,380,294 | A | 1/1995 | Persson |
| 5,413,562 | A | 5/1995 | Swauger |
| 5,685,859 | A | 11/1997 | Kornerup |
| 5,693,032 | A | 12/1997 | Bierman |
| 5,810,781 | A | 9/1998 | Bierman |
| 5,833,667 | A | 11/1998 | Bierman |
| 5,885,254 | A | 3/1999 | Matyas |
| 5,897,519 | A | 4/1999 | Shesol et al. |
| 5,947,931 | A | 9/1999 | Bierman |
| 6,113,577 | A | 9/2000 | Hakky et al. |
| 6,231,548 | B1 | 5/2001 | Bassett |
| 6,273,873 | B1 | 8/2001 | Fleischer |
| 6,290,676 | B1 | 9/2001 | Bierman |
| 6,302,867 | B1 | 10/2001 | Brown, Jr. et al. |
| 6,311,933 | B1 | 11/2001 | Starchevich |
| 6,428,515 | B1 | 8/2002 | Bierman et al. |
| 6,582,403 | B1 | 6/2003 | Bierman et al. |
| 6,673,046 | B2 | 1/2004 | Bierman et al. |
| 7,014,627 | B2 | 3/2006 | Bierman |
| 7,018,362 | B2 | 3/2006 | Bierman et al. |
| 7,119,247 | B2 | 10/2006 | Worthley |
| 7,153,291 | B2 | 12/2006 | Bierman |
| 7,220,246 | B2 | 5/2007 | Raulerson et al. |
| D547,862 | S | 7/2007 | Dikeman et al. |
| 7,413,561 | B2 | 8/2008 | Raulerson et al. |
| 2002/0188255 | A1 | 12/2002 | Bierman et al. |
| 2005/0027258 | A1 | 2/2005 | Bierman et al. |
| 2006/0058738 | A1 | 3/2006 | Ponzi |
| 2006/0129103 | A1 | 6/2006 | Bierman et al. |
| 2006/0161109 | A1 | 7/2006 | Huet |
| 2006/0264836 | A1 | 11/2006 | Bierman |
| 2008/0065022 | A1 | 3/2008 | Kyvik et al. |
| 2008/0097334 | A1 | 4/2008 | Dikeman et al. |
| 2008/0171993 | A1 | 7/2008 | Beran |
| 2008/0200880 | A1 | 8/2008 | Kyvik et al. |
| 2008/0249476 | A1 | 10/2008 | Bierman et al. |
| 2009/0093769 | A1 | 4/2009 | Wright et al. |

FOREIGN PATENT DOCUMENTS

| | | |
|---|---|---|
| GB | 2 333 234 | 7/1999 |
| JP | 2003 062083 | 3/2003 |
| WO | WO 98/15312 | 4/1998 |
| WO | WO 02/11786 A2 | 2/2002 |
| WO | WO 2004/026161 | 4/2004 |
| WO | WO 2008/054761 | 5/2008 |
| WO | WO 2010/002393 | 1/2010 |

OTHER PUBLICATIONS

European Search Report dated Nov. 6, 2012 in copending European Appln. No. 12183339.
European Search Report dated Nov. 6, 2012 in copending European Appln. No. 12183340.
European Search Report dated Feb. 21, 2012 in corresponding European Appln. No. 09818393.
Written Opinion and International Search Report in International Application No. PCT/US2009/058909 filed Sep. 30, 2009.
Chinese Office Action dated Oct. 26, 2012 in copending Chinese Application No. 200980138766.
Australian Patent Examination Report dated Jan. 15, 2013 in copending Australian Application No. 2012216807.

CATHETER FIXATION DEVICE

CROSS REFERENCE TO RELATED APPLICATION

This application claims the benefit of and priority to Japanese Patent Application Serial No. 2011-213481 which was filed Sep. 28, 2011, the entirety of which is incorporated herein by reference.

BACKGROUND

1. Technical Field

The present invention relates to a catheter fixture for fixing a catheter to the skin of a patient.

2. Description of Related Art

The use of catheters has been widely implemented in recent years for treatment and diagnosis in medical facilities. This type of catheter requires that a tip part of the catheter be securely held to the appropriate area for treatment or diagnosis and is therefore generally fixed to the patient by an external part exposed outside of the skin.

Catheter fixtures for fixing a catheter to the surface of the skin of a patient have been conventionally proposed as a means for fixing a catheter to a patient. This type of catheter fixture is provided with, for example, a fixture main body made of a soft resin and a fixing member made of a metal or resin having higher rigidity than the fixture main body.

A retention part is provided on the fixture main body having an arrangement that allows for the catheter to be inserted. When configuring an insertion arrangement for the catheter, nearly the entire circumference of the catheter is covered by the retention part. The fixing member is covered from the upper direction of the fixture main body to provide sufficient reinforcing effect for the fixture main body. As a result, the catheter is fixed as the retention part is tightened.

Note, there are several other proposals for related art for this type of catheter fixture. See, e.g., Japanese Unexamined Application Publication 2003-154012 and Japanese Unexamined Patent Application Publication 2008-212434. In addition to those configured with a separate fixture main body from the fixing member, there are also those that are integrated by being mutually linked.

However, with the conventional catheter fixture, pressure is applied to the skin when the fixing member is engaged by covering from a perpendicular direction of the fixture main body. Therefore, there is the problem that the patient experiences a physical burden as the skin is compressed.

Further, there is also the risk of losing one of the compositional pieces when the conventional catheter fixture is composed of a fixture main body and a separate fixing member. Furthermore, conventional catheter fixtures have the weakness of not being able to obtain the recommended state as there is the risk of fixing by only using the fixture main body without using the fixing member.

In addition, with the conventional catheter fixture that is integrated by mutually linking the fixture main body and the fixing member, the two compositional components are merely linked by, for example, a strap or the like. It does nothing more than achieve an effect of loss prevention. Therefore, there remains room for improvement.

An object of the present invention, upon consideration of the problems described above, is to provide a catheter fixture that can stably fix a catheter to a patient without causing much of a burden to the patient at the time of fixing and which has no concern for losing the compositional components.

SUMMARY

The following embodiments 1 to 6 are given for resolving the problems described above.

According to one embodiment, a catheter fixture for fixing a tubular catheter to a patient comprises a plate shaped fixture main body having a pair of winged pieces and a retention part in which a catheter retaining groove is formed. A fixing member is configured separately from the fixture main body that can cover the catheter retaining groove. A pivot connecting shaft is provided that both connects the fixture main body and the fixing member and acts as the pivot axis of the fixing member. The catheter is fixed by the pivoting action of the fixing member along a horizontal plane direction of the fixture main body centrally around the pivot connecting shaft thereby covering the catheter retaining groove with the fixing member.

Therefore, with the invention according to embodiment 1, the fixing member can be moved to pivot along the horizontal plane direction of the fixture main body centrally around the pivot connecting shaft that also acts as the pivot axis. By this action, the catheter is stably fixed because the catheter retaining groove is covered by the fixing member. At this time, the fixing member is pressed along the horizontal plane direction of the fixture main body and therefore a pressing force in a perpendicular direction to the skin is difficult. Therefore, the catheter can be fixed without causing much of a burden to the patient. In addition, losing the compositional components can be prevented because the fixture main body configured separately is integrally coupled with the fixing member by the pivot connecting shaft.

In a second embodiment, the catheter fixture according to embodiment 1, also includes a retention part that is pressed by the fixing member upon completion of the pivoting action by the fixing member thereby narrowing the catheter retaining groove.

With the invention according to embodiment 2, the retention part is pressed by the fixing member and the catheter retaining groove narrows, and as a result, the catheter is tightened by the retention part to be stably and firmly fixed.

In a third embodiment, the catheter fixture according to embodiments 1 or 2 includes a guide part with a plan view arc shape provided on the retention part of the fixture main body, and a guided part with a plan view arc shape with the ability to lock with the guide part provided on the free end side of the fixing member.

With the invention according to embodiment 3, because the guided part has the ability to lock with the guide part, the fixing member is guided along a horizontal plane direction of the fixture main body so that the fixing member can be smoothly pivoted centrally around the pivot connecting shaft. In addition, when the fixing member arrives at the pivot completion position, the fixing member is difficult to release from the fixture main body.

In a fourth embodiment, the catheter fixture according to any one of embodiments 1 to 3 includes a pivot connecting shaft that is provided in a cylindrical shape on the fixing member, and the pivot connecting shaft is axially supported with the ability to pivot within a through hole formed on the wing piece.

With the invention according to embodiment 4, because the pivot connecting shaft is axially supported by utilizing the through hole formed in the wing piece, there is no need to provide a structural part for axial support separately which makes it easier to avoid complicating the structure and increasing the cost. In addition, because the pivot connecting shaft has a cylindrical shape, the function as a through hole can be substantially maintained without blocking that portion even when being axially supported by the through hole. Furthermore, with this configuration, there can be comparatively high rigidity in the pivot axis portion.

In a fifth embodiment, the catheter fixture according to any one of embodiments 1 to 4 includes an upper surface of the retention part of the fixture main body that slides in contact with the undersurface of the fixing member during the pivoting action and a raised ridge part that is provided to protrude to lift up the fixing member as it passes by.

With the invention according to embodiment 5, when the fixing member during the pivoting action passes by a location that has a raised ridge part, the fixing member is lifted up because the upper end of the raised ridge part slides in contact with the undersurface of the fixing member. Therefore, the catheter arranged in the catheter retaining groove can be avoided when pivoting the fixing member making it difficult for the fixing member to get caught on the catheter. In addition, by providing a raised ridge part, the direction to pivot the fixing member can be easily understood.

In a sixth embodiment, the catheter fixture according to embodiment 5 includes a recessed part, which has the ability to engage with the raised ridge part upon completion of the pivoting action by the fixing member, provided on the undersurface of the fixing member.

With invention according to embodiment 6, the recessed part engages with the raised ridge part when the recessed part of the fixing member arrives at the position of the raised ridge part of the fixture main body. At such time, because the operator receives a click sensation at the fingertip, it can be understood by a tactile impression that the pivoting action is completed and the catheter fixture is in a complete fixed state.

As described in detail above, with the invention according to embodiments 1-6, a catheter fixture can be provided that can stably fix a catheter without causing much of a burden to the patient at the time of fixing and which has no concern for losing the compositional components.

BRIEF DESCRIPTION OF THE DRAWINGS

FIG. 1(a) is a perspective view illustrating a fixture main body of a catheter fixture in one embodiment of the present invention, (b) is a plan view illustrating the fixture main body shown in FIG. 1(a), (c) is a front view illustrating the fixture main body shown in FIG. 1(a), (d) is a bottom view illustrating the fixture main body shown in FIGS. 1(a), and (e) is a side view illustrating the fixture main body shown in FIG. 1(a);

FIG. 2(a) is a bottom perspective view of the fixing member of the presently disclosed catheter fixture, (b) is a plan view illustrating the fixing member shown in FIG. 2(a); (c) is a front view illustrating the fixing member shown in FIGS. 2(a), and (d) is a side view illustrating the fixing member shown in FIG. 2(a);

FIG. 3(a) is a plan view illustrating the state at the time of the start of the pivoting action of the fixing member in relation to the fixture main body of the catheter fixture, (b) is a front view of the catheter fixture shown in FIGS. 3(a); and (c) is a perspective view looking from above of the catheter fixture shown in FIG. 3(a);

FIG. 4(a) is a plan view illustrating the state during the pivoting action of the fixing member in relation to the fixture main body of the catheter fixture, (b) is a front view of the catheter fixture shown in FIG. 4(a); (c) is a perspective view looking from above of the catheter fixture shown in FIG. 4(a).

FIG. 5(a) is a plan view illustrating the state of the catheter device after completion of the pivoting action of the fixing member in relation to the fixture main body of the catheter fixture, (b) is a front view of the catheter fixture shown in FIGS. 5(a), (c) and (d) are perspective views looking from above of the catheter fixture shown in FIG. 5(a).

DETAILED DESCRIPTION

A description will be provided hereinafter in detail of a catheter fixture 11 of a specific embodiment of the present invention based on FIG. 1 to FIG. 5.

Figure 4:
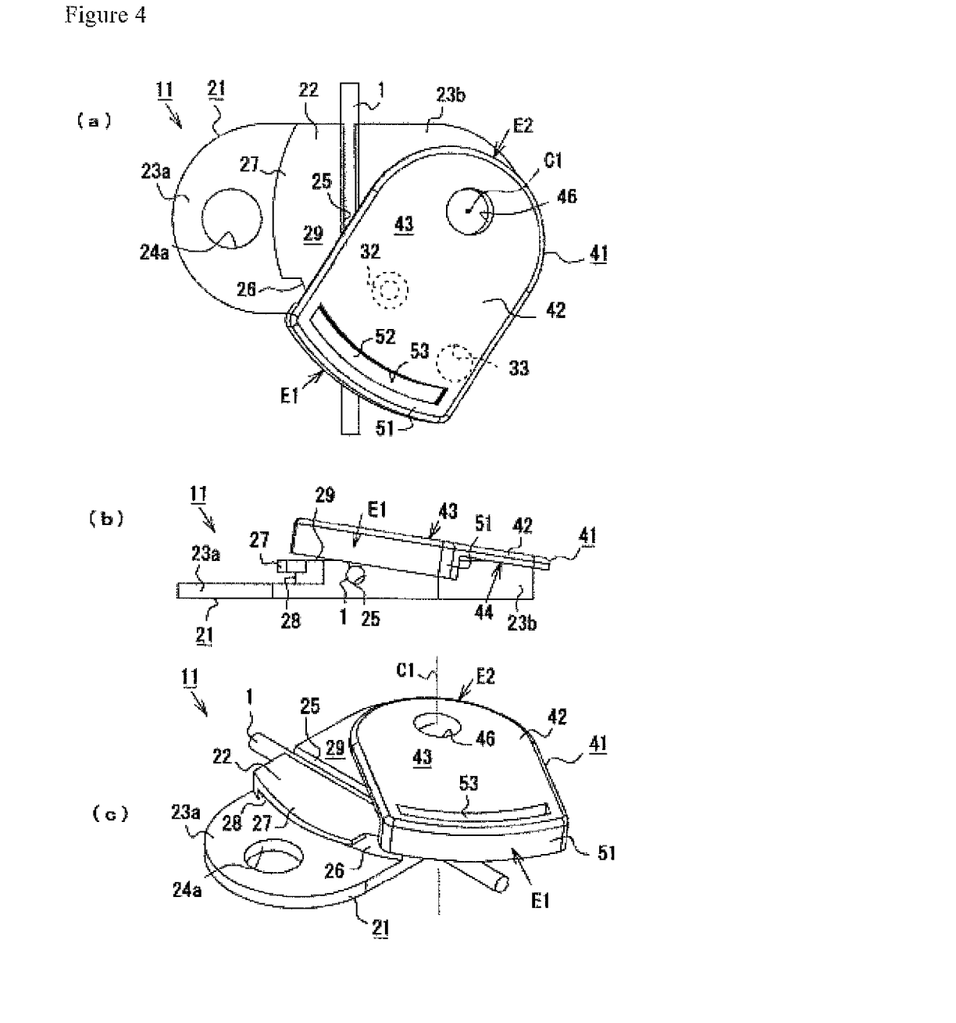
Figure 5:
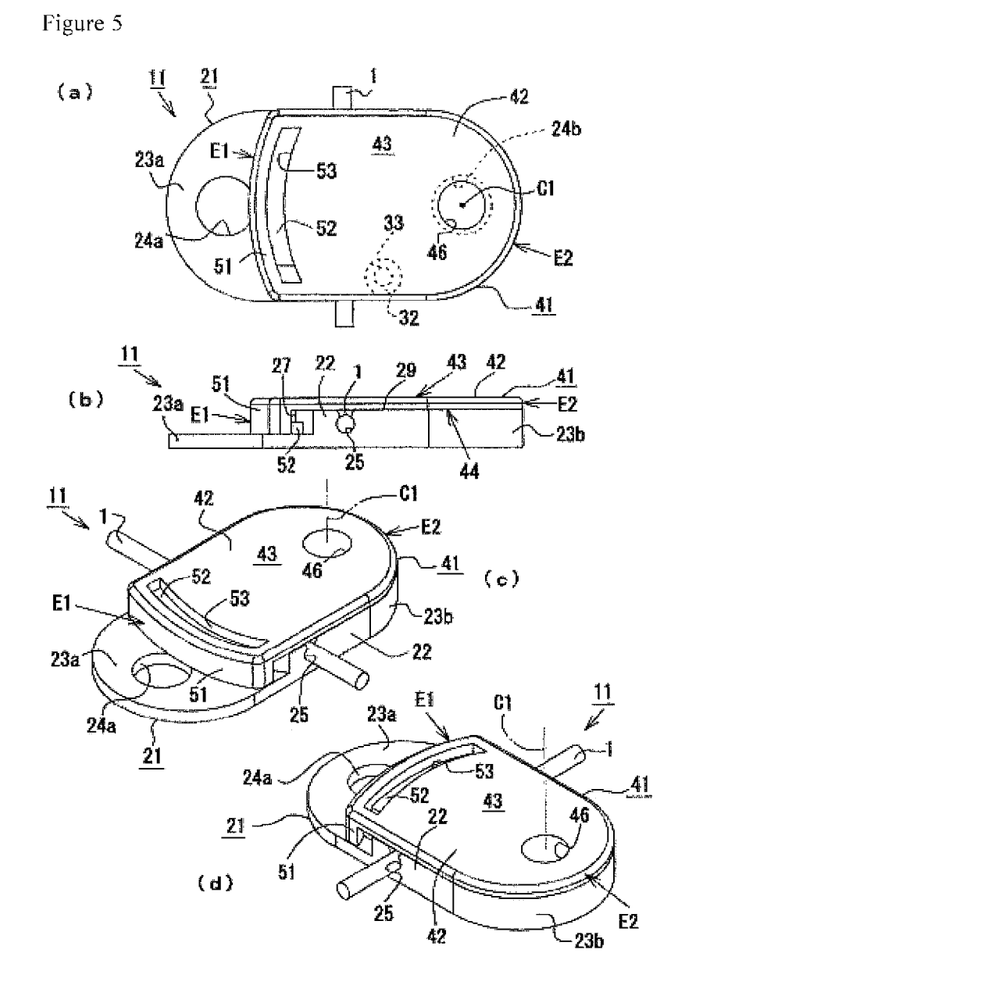

The catheter fixture 11 of the present embodiment is a medical instrument used for fixing a tubular catheter 1 to the skin of a patient. The catheter fixture 11 is fundamentally composed of two components (a fixture main body 21 and a cover 41 as a fixing member) as illustrated in FIG. 3 to FIG. 5.

Figure 1:
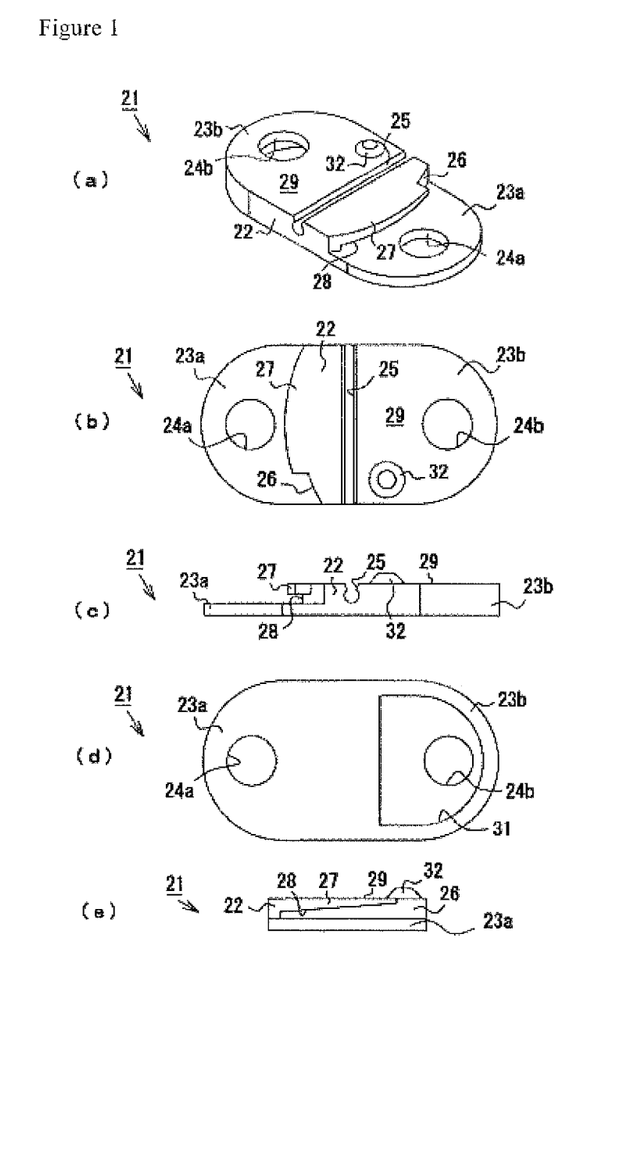
Figure 3:
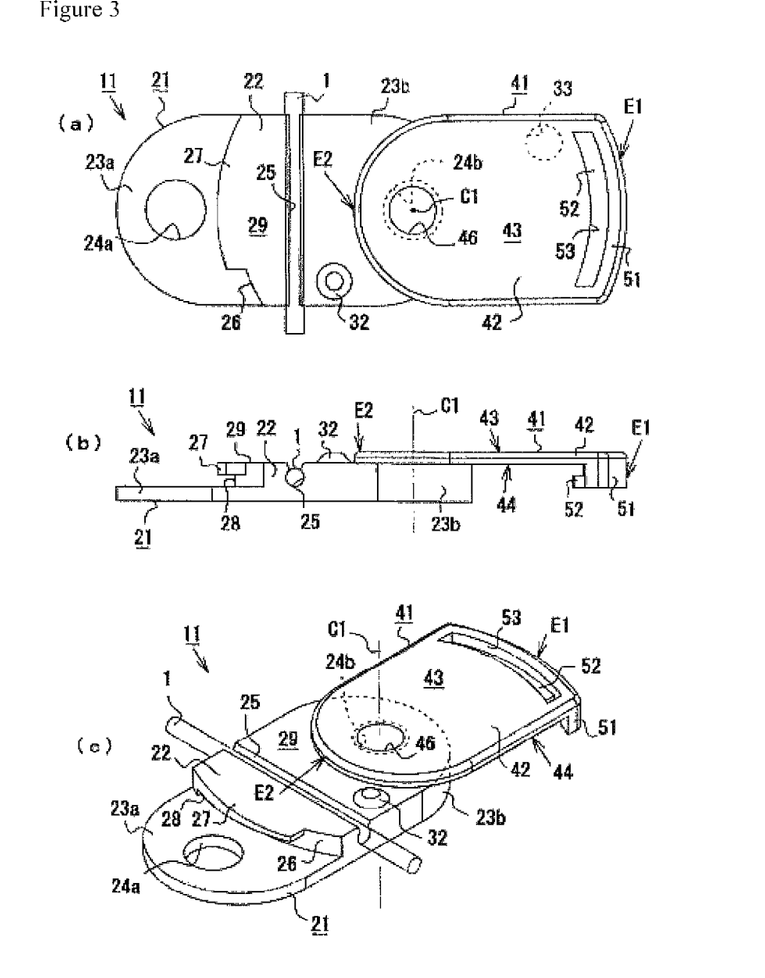

As illustrated in FIG. 1, FIG. 3, and the like, the fixture main body 21 is a plate shaped member with a plan view oval shape and is formed by using a relatively soft synthetic resin material (for example, a polyamide elastomer). In addition to a polyamide elastomer, a soft synthetic resin material, for example, polyvinyl chloride, silicone rubber, flexible polyurethane, polyamide elastomer, or the like may be selected. Here, because the fixture main body 21 is the member that directly contacts the skin, a material is preferred that has flexibility and elasticity in order to relieve a sense of discomfort given to the patient. Further, the synthetic resin material forming the fixture main body 21 is preferably softer than the tubular material of the catheter 1. The reason for this is to prevent the catheter 1 from being distorted when a compressing force is applied to the catheter 1 while the catheter 1 is held to the fixture main body 21 which may cause the inner cavity of the catheter 1 to collapse.

The fixture main body 21 has a pair of wing pieces 23a and 23b. Circular holes 24a and 24b are provided in these wing pieces 23a and 23b. These holes 24a and 24b are through holes for inserting sutures. In addition, an adhesive layer to adhesively secure the fixture main body 21 to the skin may be formed on the rear surface side of the fixture main body 21 by applying an adhesive agent or pasting an adhesive sheet. A release film may be laminated to protect the adhesive layer in the state of prior to use. As illustrated in FIG. 1(d), a D-shaped recessed part 31 is provided in the region that includes the hole 24b on the undersurface side of the wing piece 23b.

A retention part 22 that is formed thicker than the other parts on the fixture main body 21, is arranged on the upper surface side of the fixture main body 21. On the fixture main body 21, the retention part 22 occupies a portion of the wing piece 23a and the entirety of the wing piece 23b. A catheter retaining groove 25 that can hold the catheter 1 is formed on the retention part 22. The catheter retaining groove 25 extends along the direction across the fixture main body 21, while at the same time, opening on the upper surface side of the fixture main body 21. Note, the cross-sectional shape of the catheter retaining groove 25 is not restricted, and in the present embodiment has a shape where a portion narrows.

As illustrated in FIG. 1, FIG. 3, and the like, an arc shaped region 27 is provided in a position on the retention part 22 between the hole 24a and the catheter retaining groove 25. A notch part 26 is formed on one end of the arc shaped region 27 to become an introduction portion for when the cover 41 engages. As illustrated in FIGS. 1(a), (c), and (e), a guide groove 28 is formed on the bottom side portion of the arc shaped region 27 as a guide part with a plan view arc shape. The guide groove 28 is formed so as to gradually narrow when proceeding in the direction along the arc (see FIG. 1(e)).

Figure 2:
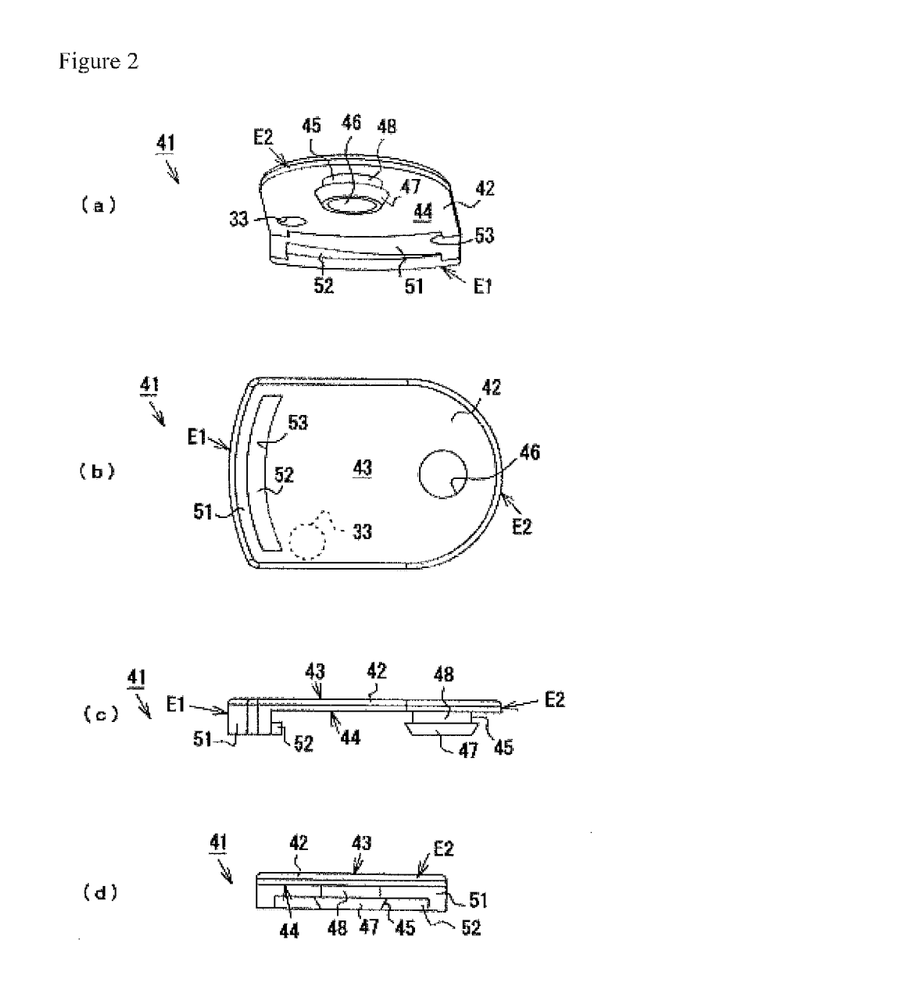

The cover 41 is illustrated in FIG. 2, FIG. 3, and the like, as the fixing member. The cover 41 is formed by using a synthetic resin material (for example, polypropylene) that is harder than the synthetic resin material composing the fixture main body 21. In addition to polypropylene, hard synthetic resin materials such as polyethylene, polycarbonate, polyamide, polyester, polyoxymethylene, rigid polyurethane, ABS, and the like, may be selected. The cover main body 42 that has a plate shape and configures the cover 41 has a top surface 43 and undersurface 44 that is arranged to contact with the upper surface 29 of the retention part 22. The cover 41 has a size that enables it to cover the entirety of the retention part 22 in a state in which the undersurface 44 side contacts the top surface 29 of the retention part 22. Note, the cover 41 in the present embodiment is a component of the size that is slightly larger than the retention part 22 but is about ¾ the size of the fixture main body 21.

As illustrated in FIGS. 2(a), (c), and (d), a pivot connecting shaft 45 is integrally provided to protrude on the center part of the fixed end E2 of the cover 41 and the undersurface 44 side of the cover 41 while also acting as a pivot axis C1. The pivot connecting shaft 45 is a cylindrical shape having a center hole 46, and is configured by a small diameter part 48 and a large diameter part 47 in a tapered shape positioned on the tip thereof. The pivot connecting shaft 45 can be mounted to fit in the hole 24b of the fixture main body 21. When the pivot connecting shaft 45 is mounted in the hole 24b, the cover 41 is supported with the ability to pivot in relation to the fixture main body 21. Further, the large diameter part 47 of the pivot connecting shaft 45 is positioned on the recessed part 31 of the undersurface 44 of the cover 41 so as to prevent the pivot connecting shaft 45 from coming off.

Meanwhile, FIG. 2(a) to (d) illustrate an arc shaped ridge 51 along the edge part of the free end E1 that is provided on the undersurface 44 side on the free end E1 side of the cover 41 which is on the opposite side of the fixed end E2. A guided ridge part 52 as a guided part with a plan view arc shape is integrally formed on the lower part of the side surface facing the fixed end E2 on the arc shaped ridge 51. The upper surface of the guided ridge part 52 is gently sloped from one end toward the other end on the arc (see FIG. 2(a)). Further, the guided ridge part 52 can engage and disengage with the guide groove 28 with a plan view arc shape. In addition, a slit shaped opening 53 is formed in a position directly above the guided ridge part 52 on the cover main body 41.

FIGS. 1(a), (b), (c), and (e) illustrate a raised ridge part 32 with a cross-section platform shape to a cross-section semispherical shape protruding in a prescribed location on the upper surface 29 of the retention part 22 of the fixture main body 21. The raised ridge part 32 functions to lift the cover 41 as it passes by in sliding contact with the undersurface 44 of the cover 41 during the pivoting action. More specifically, the raised ridge part 32 is on the upper surface 29 of the retention part 22 and is arranged in a position between the catheter retaining groove 25 and the hole 24b on the side where the pivot connecting shaft 45 is supported. Moreover, because the notch part 26 is the introduction portion when engaging with the cover 41, the raised ridge part 32 is positioned to sandwich the catheter retaining groove 25 just at the opposite side of the notch part 26. Meanwhile, FIGS. 2(a) and (b) illustrate the recessed part 33 that has the ability to engage and disengage with the raised ridge part 32 upon completion of the pivoting action of the cover 41. Recessed part 33 is provided in a position that accommodates the raised ridge part 32 on the undersurface 44 side of the cover 41.

Next, a description will be provided of the procedure to fix the catheter 1 by using the catheter fixture 11 of the present embodiment configured as described above based on FIG. 3 to FIG. 5.

For example, in one embodiment, the catheter 1 percutaneously leads to the subclavian vein, and the remainder of the catheter 1 is led outside the skin from the puncture site of the precordial region of the patient. Further, the catheter fixture 11 is attached to an area outside the body and the catheter 1 is led outside of the skin. In the initial state, as illustrated in FIG. 3(a) to (c), the free end E1 of the cover 41 is in a position greatly removed from the catheter retaining groove 25, and the catheter retaining groove 25 is completely exposed.

First, the outside of the body part of the catheter 1 is inserted in the catheter retaining groove 25 formed by the retention part 22 of the fixture main body 21 (see FIG. 3(a) to (c)). If there is an adhesive layer on the under surface side of the fixture main body 21, the fixture main body 21 may be adhered to the skin with the adhesive layer at this stage.

Next, the cover 41 is held by the fingers and pivoted in a clockwise direction of FIG. 4(a) centrally around the pivot connecting shaft 45. At that time, the operator can easily understand from looking at the raised ridge part 32 which direction to rotate the cover 41. When the cover 41 passes by the location where the raised ridge part 32 is during the pivoting action, the cover 41 is lifted up by the sliding contact of the upper end of the raised ridge part 32 on the undersurface 44 of the cover 41 (see FIG. 4(a) to (c)). Accordingly, the lower end of the arc shaped ridge 51 that projects out at the undersurface 44 side of the cover 41 is temporarily in a higher position than the catheter 1 arranged on the catheter retaining groove 25. Therefore, the cover 41 can be pivoted to avoid the catheter 1 making it difficult for the arc shaped ridge 51 to get caught on the catheter 1.

Furthermore, when further pivoting the cover 41 for one end of the guided ridge part 52 to arrive at the notch part 26, it is gradually introduced into the guide groove 28 from that position. At this time, it is smoothly guided by the sliding contact of the guided ridge part 52 along the guide groove 28. When the cover 41 is in a state so as to entirely cover the retention part 22 and the catheter retaining groove 25 (in other words, the state upon completion of the pivoting action), the recessed part 33 arrives at the position of the raised ridge part 32, and the raised ridge part 32 engages with the recessed part 33 (see FIG. 5(a) and the like). At such time, because the operator receives a click sensation at the fingertip, it can be understood by a tactile impression that the pivoting action has completed and is in a complete fixed state. Note, the cover 41 cannot be pivoted beyond that position. However, the cover 41 is configured so as not to cover the hole 24a provided on the other wing piece 23a.

When arriving at this type of state, the inner surface of the guide groove 28 on the retention part 22 is pressed in the direction of the catheter retaining groove 25 by the tip end surface of guided ridge part 52 on the cover 41. A deformation occurs in the retention part 22 according to this pressing, and the catheter retaining groove 25 narrows. As a result, the outside of the body part of the catheter 1 is tightened by the retaining part 22 to be stably and firmly fixed. Furthermore, when in the completely fitted state, the undersurface 44 the cover 41 and the upper surface 29 of the retention part 22 are in contact and the retention part 22 is nearly completely covered by the cover 41. Thereafter, dressing may be applied as necessary to the catheter fixture 11 and the puncture site for protection.

Further, when it is desired to release the catheter 1 from the catheter fixture 11, the opposite action as the pivoting action described above is performed. If dressing has been applied, then first remove the dressing to expose the catheter fixture 11. At that time, while applying additional force upward on the catheter fixture 11 is easy, it is difficult to apply force in the direction for removing the cover 41, and therefore there is very little risk of removing the cover 41 together with the dressing. Further, the fact that the guided ridge part 52 is locked with the guide groove 28 and that the pivot connecting shaft 45 is mounted in the hole 24b contributes to removal prevention of the cover 41. Next, the cover 41 is pivoted in a counterclockwise direction thereby exposing the catheter retaining groove 25. At that time, the catheter retaining groove 25 that had narrowed by the pressure of the retention part 22 is widened to release the fix on the catheter 1, and the catheter 1 can be removed.

The following effects can be obtained according to the present embodiment.

(1) According to the configuration of the catheter fixture 11 of the present embodiment, the cover 41 can be pivoted along the horizontal plane direction of the fixture main body 21 centrally around the pivot connecting shaft 45 that also acts as the pivot axis C1. By this action, the catheter 1 is stably fixed because the catheter retaining groove 25 is covered by the cover 41. At this time, the cover 41 is pressed along the horizontal plane direction of the fixture main body 21 and therefore a pressing force in a perpendicular direction to the skin is difficult. Therefore, the catheter 1 can be fixed without causing much of a burden to the patient. Further, it differs from the conventional catheter fixture that is integrated by mutually linking the fixture main body and the fixing member by a strap and is superior in that it achieves an effect above that of loss prevention.

(2) In addition, losing the compositional components can be prevented because the fixture main body 21 configured separately is integrally coupled with the cover 41 by the pivot connecting shaft 45. Therefore, it differs from the conventional catheter fixture that is composed separately of a fixture main body and a fixing member in that there is no risk of fixing the catheter 1 by using only the fixture main body 21 without using the cover 41. Therefore, it is superior in that the recommended fixed state can be securely obtained.

(3) According to the configuration of the catheter fixture 11 of the present embodiment, it is difficult to apply a force in the direction of removing the cover 41 even when removing a dressing. Therefore, it is superior in that an unexpected circumstance is difficult to occur together with the removal, and the like, of the cover 41.

(4) According to the configuration of the catheter fixture 11 of the present embodiment, as a result of the inner surface of the guide groove 28 pressing in the direction of the catheter retaining groove 25 by the tip end surface of the guided ridge part 52 upon completion of the pivoting action of the cover 41, the catheter retaining groove 25 can be narrowed. As a result, the outside of the body part of the catheter 1 is tightened by the retaining part 22 to be stably and firmly fixed.

(5) According to the configuration of the catheter fixture 11 of the present embodiment, the guided ridge part 52 which is the guided part to the guide groove 28 as the guide part can be locked. Therefore, the cover 41 is guided along the horizontal plane direction of the fixture main body 21, and the cover 41 can be smoothly pivoted centrally around the pivot connecting shaft 45. In addition, when the cover 41 arrives at the pivot completion position, the cover 41 is difficult to release from the fixture main body.

(6) According to the configuration of the catheter fixture 11 of the present embodiment, the pivot connecting shaft 45 is axially supported by utilizing the hole 24b formed on one side of the wing piece 23b. Therefore, there is no need to provide separate structural components for support. Thus, a complicated structure which results in increased cost can be avoided. In addition, because the pivot connecting shaft 45 is in a cylindrical shape, the function as a through hole for inserting sutures can be substantially maintained without blocking that portion even when being axially supported by the hole 24b. Furthermore, with this configuration, there can be comparatively high rigidity in the pivot axis C1 portion. Therefore, a compressing force by the cover 41 can be effectively applied, and the catheter retaining groove 25 can be securely narrowed from a lateral direction and tightened. In addition, according to this type of pivot axis structure, because the pivot connecting shaft 45 basically does not bring about any deformation, the cover 41 can smoothly be pivoted while tracing the correct route.

(7) Because the catheter fixture 11 of the present embodiment forms a state in which the under surface 44 of the cover 41, which is the fixing member, is in contact with the upper surface of the retention part 22, the overall thickness of the catheter fixture 11 can be securely suppressed. In addition, because the retention part 22 is entirely covered by the cover 41, the retention part 22 and the catheter 1 held thereby are not in direct contact with the dressing. Therefore, slipping or the like of the catheter 1 in conjunction with the removal of the dressing can be prevented.

(8) With the present embodiment, because the cover 41 is made from a synthetic resin material that is harder than the fixture main body 21, the retention part 22 made of a relatively softer synthetic resin material can be effectively compressed. Therefore, the retention part 22 can securely deform so that the catheter retaining groove 25 can be securely narrowed. Thus, the catheter 1 can be more firmly tightened and fixed by the retention part 22. In addition, with the present embodiment, because the fixture main body 21 and the cover 41 are both made of a synthetic resin material without using metal material, there is the particular benefit of not needing removal even during an examination in which magnetic resonance imaging (MRI) is used.

Note, the embodiment of the present invention may be modified as given below.

Although the pivot connecting shaft 45 in the present embodiment described above has a cylindrical shape, it is not restricted to that, and can be, for example, a columnar shape without a center hole.

Although one of the holes 24a and 24b formed on the wing pieces 23a and 23b was used as a hole for supporting the pivot connecting shaft 45 in the present embodiment described above, a structural component to provide support can be provided in another location.

Although the pivot connecting shaft 45 is integrally formed on the cover main body 42 side that configures the cover 41 in the present embodiment described above, it is not restricted to that. For example, the pivot connecting shaft 45 can be integrally formed on the fixture main body 21 and a through hole for axial support can be provided on the cover 41 side. Or, the pivot connecting shaft 45 can be configured separately from the fixture main body 21 and the cover 41, and the pivot connecting shaft 45 can be inserted through a through hole for axial support respectively provided on the fixture main body 21 and the cover 41.

The horizontal plane shape of the cover 41 is not restricted to that given in the embodiment described above that can be suitably changed. For example, the cover 41 may have substantially the same outer shape and dimensions as the fixture main body 21.

The catheter retaining groove 25 is configured to narrow by pressure applied by the retention part 22 in the present embodiment described above but this does not have to be the case.

The cover 41 is made of a nontransparent resin material in the present embodiment described above, but it may also be made of a transparent resin material.

According to the catheter fixture 11 of the present embodiment described above, respective position determining markers may be provided for the fixture main body 21 and the cover 41. Therefore, according to this configuration, position determination for the fixture main body 21 and the cover 41 can be easily understood visually by having a mutual positional relationship with position determining marks.

Next, the technical concepts understood by the embodiment described above will be listed below.

(1) According to any one of the embodiments 1 to 6, both the fixture main body and the fixing member can be made of resin.

(2) According to any one of the embodiments 1 to 6, the fixing member can be made of a nontransparent resin material.

(3) According to any one of the embodiments 1 to 6, the catheter retaining groove can be arranged so to pass through the substantial center part of the fixture main body and to open on the top surface side of the fixture main body.

(4) According to any one of the embodiments 1 to 6, the fixing member can be made of a harder material than the fixture main body.

(5) According to any one of the embodiments 1 to 6, a position determining mark can be provided respectively on the fixture main body and the fixing member.

(6) According to any one of the embodiments 1 to 6, the fixing member may not stick out from fixture main body upon completion of the pivoting action.

(7) According to any one of the embodiments 1 to 6, the fixing member can be a protective cover that entirety covers the upper surface of the retention part as well as the catheter retaining groove.

(8) According to any one of the embodiments 1 to 6, the fixing member may not cover a hole provided in the wing piece upon completion of the pivoting action.

(9) According to any one of the embodiments 1 to 6, the fixture main body can be fixed to the skin.

(10) According to embodiments 5 or 6, the raised ridge part can be on the upper surface of the retention part and be arranged in a position between the catheter retaining groove and the hole on the side where the pivot connecting shaft is supported.

(11) According to embodiments 5 or 6, the raised ridge part can be positioned to sandwich the catheter retaining groove at just to the opposite side of the introduction portion when the cover is engaged.

What is claimed is:

1. A catheter fixture for fixing a tubular catheter, comprising a plate shaped fixture main body having a pair of winged pieces and a retention part in which a catheter retaining groove is formed, a fixing member configured separately from the fixture main body that can cover the catheter retaining groove, and a pivot connecting shaft that both connects the fixture main body and the fixing member and acts as the pivot axis of the fixing member; wherein the catheter is fixed by pivoting action of the fixing member in relation to the fixture main body along a horizontal plane direction of the fixture main body centrally around the pivot connecting shaft thereby covering the catheter retaining groove with the fixing member, wherein the retention part is pressed by the fixing member upon completion of the pivoting action by the fixing member thereby narrowing the catheter retaining groove.

2. The catheter fixture according to claim 1, wherein a guide part with a plan view arc shape is provided on the retention part of the fixture main body, and a guided part with a plan view arc shape with the ability to lock with the guide part is provided on a free end side of the fixing member.

3. The catheter fixture according to claim 1, wherein the pivot connecting shaft is positioned on the fixing member and has a cylindrical shape, and the pivot connecting shaft is axially supported with the ability to pivot within a through hole formed on one of the pair of winged pieces.

4. The catheter fixture according to claim 1, wherein an upper surface of the retention part of the fixture main body slides in contact with an undersurface of the fixing member during the pivoting action and a raised ridge part is provided on an upper surface of the fixture main body to lift up the fixing member as the fixing member passes over the raised ridge part.

5. The catheter fixture according to claim 4, wherein a recessed part is provided on the undersurface of the fixing member with the ability to engage with the raised ridge part upon completion of the pivoting action by the fixing member.

* * * * *